United States Patent [19]

Cobia et al.

[11] Plant 5,104

[45] Sep. 13, 1983

[54] PLANT OF THE CACTACEAE PLANT FAMILY

[75] Inventors: Barnell L. Cobia; Robert L. Cobia, both of Winter Garden, Fla.

[73] Assignee: B. L. Cobia, Inc., Winter Garden, Fla.

[21] Appl. No.: 370,554

[22] Filed: Apr. 21, 1982

[51] Int. Cl.[3] ..... A01H 5/00

[52] U.S. Cl. ..... Plt./88

[58] Field of Search ..... Plt./88

*Primary Examiner*—Robert E. Bagwill

*Attorney, Agent, or Firm*—Roger L. Martin

[57] ABSTRACT

A new and distinct plant variety of the Cactaceae family is of the type known commercially as a "Christmas Cactus" has an erect growth habit and blooms with perianth tube forming tepals that have an axially oriented crease that extends proximally from the distal ends of the tepals and perianth tube laminating and forming tepals that in the marginal blade areas are dominated with colors that have a yellow hue.

4 Drawing Figures

The invention relates to a new and distinct plant variety of the Cactaceae family and which has been named the *Zygocactus truncatus* 'Gold Charm' by the inventors.

Certain plant varieties of the Cactaceae family are well known in the foliage plant market and among these are those which are commonly referred to as the Christmas Cactus varieties because they tend to bloom during the Thanksgiving-Christmas holiday seasons.

The Christmas Cactus varieties on the market have blooms which vary in color from one variety to the next as is evident from the current U.S. patent art. However, no Christmas Cacti that are found in the marketplace are known by the inventors to provide a bloom which could be called a yellow bloom in the every day vernacular of the marketplace. Accordingly a general objective of the invention has been to develop a variety of the Cactaceae Family that has a generally "yellow" colored bloom. The objectives of the invention have been fully realized by the development of the new plant variety hereinafter described in detail. The new plant variety was developed in a nursery located at Winter Garden, Fla., as a hybrid secured by cross pollinating the flower of a plant specimen of a research variety developed by the inventors and characterized by a white bloom with pollen from a plant specimen of yet another research variety that is characterized by what may be considered as an off colored generally "yellow" bloom. The seeds taken from the fertilized seed pod were cultivated at the mentioned nursery location and after prolonged observation of the seedlings, the hybridized plant of the new plant variety was selected and asexually reproduced by the inventors at the Winter Garden nursery through the propagation of stem cuttings taken from the original hybrid plant. Both of the parental varieties are research varieties that have not appeared in the marketplace.

Through successive propagations, it has been ascertained that specimens of the new plant variety generally resemble the parent varieties but are distinguishable from these varieties and from other related varieties known to the inventors by a growth habit which is evident in plant specimens propagated and grown under nursery conditions utilized in the growing of tropical plants in Winter Garden, Fla., as combining the following principal characteristics:

1. An erect growth habit,

2. A bloom with perianth tube forming tepals that are characterized by an axially oriented crease that extends proximally from the distal end of the tepal, and a bloom with perianth tube forming and laminating tepals that in colors in the marginal areas are dominated by a yellow hue.

The accompanying drawings serve by color photographic means to illustrate the new plant variety and wherein one sheet shows two one year old specimens of the new plant variety and which were simultaneously propagated and grown from two phylloclades in a conventional 3" pot found in the marketplace and pruned to one tier of phylloclades above the propagated phylloclade after six months growth to promote breaking. Other photographs illustrate the phylloclades with an attached bloom and maturing bud. Yet another photograph is an enlargement of the bloom as seen from the abaxial side of the erect tube forming tepals while another photograph shows a bloom as sectioned generally longitudinally through the perianth tube and ovary to expose the style and stamen arrangement.

The following is a detailed description of the new plant variety with colors and hues, unless otherwise clearly indicated by the text through the absence of color notations, being named in accord with the ISCC-NBS Method of Designating Colors. (U. S. Dept. of Commerce, National Bureau of Standards, Circular 553) the named colors being interpreted from color notations derived by comparison with the color specimens of the Munsell Book of Color. The description is further based on observations of well fertilized plants of about one year of age from initial propagation and which were grown under 50–75% shaded glasshouse nursery conditions in the Winter Garden, Fla. area and wherein temperatures ranges from 60°–85° F. during the winter months and from 75°–95° F. during the summer months, and are ambient during the intervening periods.

DETAILED PLANT DESCRIPTION

Name: *Zygocactus truncatus* 'Gold Charm'.

Parentage:

A. *Maternal*.—ZH1178T, an unnamed and unmarked variety with a generally "white" bloom.

B. *Paternal.*—ZH15139, an unnamed and unmarketed variety with an off color generally "yellow" bloom.

Classification:

A. *Botanic* (Britton and Rose, *The Cactaceae,* Constable and Co., Ltd., London 1937, Vol. IV).—

| | | |
|---|---|---|
| (1) | Family: | Cactaceae |
| (2) | Tribe: | Cereeae |
| (3) | Sub-tribe: | Epiphyllanae |
| (4) | Genus: | Zygocactus |
| (5) | Species: | Truncatus (Haworth) Schumann |

B. *Commercial.*—Thanksgiving-Christmas season blooming cactus.

Form: Epiphylic and terrestrial, shade loving, succulent, leafless plant with jointed and branched stems.

Stems:

A. *General.*—Irregular with usually multichotomous branching of upright, adventitiously rootable, flattened phylloclades that have a prominent midrib and prominently toothed lateral wings.

B. *Phylloclades.*—(1) General: Elongated and flat with a transversely elongated, areole bearing, truncated apex, with inwardly tapering basal wing margins that merge with a broad pointed basal juncture with the phylloclade therebelow, and with an axially located areole associated with each tooth. (2) Midrib: (a) General — Extends longitudinally of phylloclade and continuously through joints with laterally tapering cortex at wing insertions. Pith surrounding vascular bundles that branch and provide lateral extensions of the vascular system to the marginal teeth. (b) Texture — Smooth, waxy epidermis with wax in small embedded scales and becoming corky in basal stem areas with age. (c) Size (at maturity) — 1. Length: Usually between 35 and 70 mm. 2. Thickness: Usually between 2 and 10 mm. (d) Color (at maturity) — Commonly moderate yellow green (7.5 GY 5/6), and/or moderate olive green (7.5 GY 3/4) (7.5 GY 4/4) (7.5 GY 4/6). (3) Wings: (a) Shape — Generally flattened with a more or less uniform taper from the midrib cortex to the tooth insertions. (b) Margins — Entire. (c) Texture — Succulent to leathery with smooth, waxy epidermis with the wax arranged in small embedded scales, and becoming woody and corky in the basal areas of the plant with age. (d) Size (at maturity) — 1. Thickness: About 1-2 mm. in the area intermediate the margin and midrib. 2. Width: Usually between 5 and 16 mm. as measured from the longitudinal axis of the phylloclade to the most offset lateral areole. (e) Color (at maturity) — Commonly moderate yellow green (7.5 GY 5/6), and/or moderate olive green (7.5 GY 3/4) (7.5 GY 4/4) (7.5 GY 4/6). (4) Teeth: (a) General shape — Generally flattened and tapered along margins from wing insertions to an apex having a hyaline, single cell, pointed spine with non-predictable bending. 1. Adaxial marginal shape: Usually straight to convex. 2. Abaxial marginal shape: Usually straight to concave. (b) Orientation — Usually projects distally of phylloclade base in an alternate arrangement. (c) Margins — Entire. (d) Texture — Succulent to leathery with smooth waxy epidermis having wax in small embedded scales of a densely comparable to that in the wings. (e) Size (at maturity) — 1. Thickness: Usually between 0.5 and 2 mm. 2. Areole to apex dimension (adaxial marginal side): Usually between 2 and 13 mm. for teeth located distally of basal teeth. (f) Color (at maturity) — Commonly moderate yellow green (7.5 GY 5/6), and/or moderate olive green (b 7/5 GY 3/4) (7/5 GY 4/4) (7/5 GY 4/6). (5) Areoles: (a) Terminal areole — Large, elongated, oval shaped with several acicular bristles, and several buds that may mature into either new phylloclades or flowers. The opposite ends of the areole are located adjacent to subsidiary areoles which are in turn located at the axils of the teeth that are located at the distal end of the phylloclade. (b) Axillary areoles — A few acicular bristles without glochidia but having copious, short, brownish, multi-cellular, wooly hairs. In areoles that are located below the teeth at the distal end of the phylloclade, there is usually only one bud and which is frequently latent.

Buds: Unarmored, ovid and chlorophyllous.

Flowers:

A. *General.*—Sessile, zygomorphic, usually solitary, terminal, perfect and epigynous with double hypanthium and undifferentiated whorled sepals and petals having a spiral emergence as a perianth provided with a sepaloid series of free tepals, a tube laminating series of tepals, and a tube forming series of united tepals.

B. *Sepaloid series.*—(1) General: Free tepals inserted on top of ovary. (2) Shape: Tapered from insertion to apex in outer members of whorl and grading inwardly in the whorl to provide progressively broader apices and longer base-tip dimensions. All members have sharp pointed tips and entire margins with sparse irregular teeth appearing in apex areas of inner members of the whorl. (3) Texture: Succulent and glabrous outer whorl members and grading inwardly in whorl to silken blades with fleshy basal areas. (4) Number: Usually from 5 to 8. (5) Size (at full bloom): (a) Base-tip dimension — Usually less then 30 mm. (b) Width dimension (maximum) — Usually less than 18 mm. (6) Color: Inner whorl members usually have a translucent white basal area that merges with marginal blade areas which in color are dominated by a yellow hue. Commonly light yellow (near 2.5 Y 8/6) (2.5 Y 9/6) (near 2.5 Y 8/8), moderate yellow (near 2.5 Y 8/6) (near 2.5 Y 8/8), pale yellow (2.5 Y 9/4), brilliant yellow (near 2.5 Y 8/8), strong yellow (near 2.5 Y 8/8), and/or pale orange yellow (10 YR 9/4). (7) Orientation at full bloom: Varying inwardly in the whorl from erect to recurve.

C. *Tube laminating series.*—(1) General: Tepals inserted on top of ovary and basally united below the throat as outer laminations on the perianth tube and with progressively greater amounts of basal fusion inwardly in the whorl. (2) Shape: Grading inwardly in the whorl with progressively longer base-tip dimensions and with progressively broader apices so that the blade area changes from ovate inwardly to spatulate with acute tip area. Entire margins with very sparse irregular teeth in the apex areas. (3)

Texture: Succulent, slightly fleshy basal areas with thin silken blades. (4) Number: Usually 4–8. (5) Size (at full bloom): (a) Base-tip dimension — Usually between 16 and 60 mm. (b) Width dimension (maximum — Usually between 14 and 20 mm. (6) Color: Marginal blade areas are in color dominated by an orange hue that merges with a translucent white basal area. Commonly yellowish white (5 Y 9/1) (10 YR 9/1) (near 2.5 Y 9/2) and/or pale yellow (near 2.5 Y 9/2) in basal areas and light yellow (5 Y 9/6) (2.5 Y 9/6) (near 2.5 Y 8/6), pale yellow (2.5 Y 9/4), and/or moderate yellow (2.5 Y 8/6) in the marginal areas of the blade. (7) Orientation: Acute to recurve.

D. *Tube forming series.*—(1) General: Tepals basally united to form hollow perianth tube that is inserted on an ovary and equipped with irregular carina (keel) at the throat. (2) Shape: (a) Perianth tube — Elongated and ellipsoidal in cross section with the major axis usually perpendicular to the phylloclade. (b) Blades — Nearly zygomorphic and thinly spatulate with acute tips. Entire margins with sparse irregular teeth in apex area. (c) Carina (keel) — Irregular and transcending. (3) Texture: (a) Perianth tube — Thick, succulent and slightly ribbed. (b) Blades — Translucent and silken. (c) Carina (keel) — Fleshy. (4) Blade number: Usually 9–11. (5) Size: (a) Perianth tube — 1. Length (base to keel): Usually between 34–40 mm. along the axis of the tube. 2. Major axis (at throat): Usually between 11–14 mm. when measured perpendicular to axis at the interior of the perianth tube. 3. Minor axis (at throat): Usually between 6–10 mm. when measured perpendicular to the axis at the interior of the perianth tube. (b) Blades — 1. Length (keel to tip): Usually between 21 and 33 mm. 2. Width (maximum): Usually between 11 and 16 mm. (6) Color (at full bloom): (a) Perianth tube — Translucent white. (b) Blades — Translucent white basal area with marginal areas being dominated in colors with a yellow hue and which merge with the translucent white basal area. Commonly light yellow (2.5 Y 9/6) (5 Y 9/6) (near 2.5 Y 8/8), yellowish white (5 Y 9/1), moderate yellow (near 2.5 Y 8/8), brilliant yellow (near 2.5 Y 8/8) and/or strong yellow (near 2.5 Y 8/8). (c) Carina (keel) — Commonly deep purplish pink (5 RP 6/10) (7.5 RP 6/10). (7) Orientation (at full bloom): Erect to recurve.

E. *Androecium (stamens).*—(1) General: Numerous exserted and diadelphous stamens with one group having filaments basally fused to the perianth tube and the other group having filamenths basally united to form a nectary housing, thin annulus around the style which is provided with a thin, deflexed, irregularly toothed margin or ruffle at the throat of the annulus. (2) Stamen number: (a) Tube attached group — Usually between 85 and 110. (b) Basally united group — Usually between 15 and 25. (3) Filaments: (a) General — Translucent and glabrous with anther connective. (b) Shape — Long, slender and terete. (c) Texture — Glabrous and silken. (d) Color — Translucent white. (e) Size — 1. Length: a. Tube attached group — Usually between 40 and 75 mm. b. Basally united group — Usually between 40 and 60 mm. 2. Diameter: Usually between 0.4 and 0.7 mm. intermediate the opposite ends. (4) Anthers: (a) General — Adnate with four longitudinally dehiscent pollen sacs and connective inserted at end. (b) Shape — Elongated. (c) Texture — Waxy. (d) Color (before dehiscence) — Commonly light yellow (5 Y 9/6) (5 Y 9/7) and/or pale yellow (5 Y 9/4).

F. *Gynoecium (pistil).*—(1) General: Compound, pariental placentation with united sytle surrounded by annular diffuse nectary at its insertion. (2) Style: (a) General — Stout and inserted in ovary. (b) Shape — Elongated, cylindrical and very slightly tapered towards stigma. (c) Texture — Fleshy and smooth. (d) Color — Commonly strong reddish purple (near 2.5 RP 4/10). (e) Size (at full bloom — 1. Length: Usually between 60 and 75 mm. 2. Diameter: Usually between 0.9 and 1.4 mm. intermediate the opposite ends. (3) Stigma: (a) General — Exserted and erect with usually 6 to 8 marginally adhering lobes. (b) Shape — Elongated and tapering toward the lobe tips with the lobes having relatively blunt apices. (c) Texture — Fleshy and smooth with the inner sides of the lobes having short glutinous capillary hairs. (d) Color — Commonly moderate purplish red (near 10 RP 5/8) (near 7.5 RP 5/8). (e) Size (lobe length at full bloom — Usually about 3.5–4 mm. along inner margins. (4) Ovary: (a) General — Epigynous with thin epidermis and distally located concavity and with a single cavity having 5 or 6 carpels with numerous ovules. (b) Shape — Ovid and gradually broadening from insertion to floral end. Ribbed single concavity with inserted style. (c) Texture — Succulent with glabrous thin outer epidermis. (d) Color — Commonly moderate greenish yellow (near 10 Y 7/8) (10 Y 7/6), strong greenish yellow (near 10 Y 7/8), moderate yellow green (2.5 GY 5/6) (2.5 GY 6/6) and/or strong yellow green (2.5 GY 7/8). (e) Size (at full bloom — 1. Length: Usually between 8 to 12 mm. between the insertion and concavity base. 2. Major axis (distal end of concavity): Usually about 11 mm. 3. Minor axis (distal end of concavity): Usually about 7 mm.

Growth habit: Erect.

The following is a general description of a one year old specimen of the new plant variety that was grown from the propagation of a single phylloclade at a nursery at Winter Garden, Fla., the specimen having been pruned to one tier above the original propagated phylloclade about six months following the initial propagation.

Age of plant: 12 months from initial propagation.
Branches from propagated phylloclade: 2.
Total number of mature phylloclades on branches grown from propagated phylloclade: 14 mature phylloclades and 19 immature phylloclades.

| | General: | | |
|---|---|---|---|
| Branch No. | No. of Phylloclades | Max. Length | No. of Tips |
| 1 | 12 | 167 mm. | 5 |
| 2 | 11 | 178 mm. | 4 |

-continued

| Midribs (mature phylloclade): | | |
|---|---|---|
| Branch No. | Length (avg.) | Thickness (avg.) |
| 1 | 52 mm. | 4.1 mm. |
| 2 | 52 mm. | 4.0 mm. |

| Wings (mature phylloclade): | | |
|---|---|---|
| Branch No. | Center Thickness (avg.) | Max. Width (avg.) |
| 1 | 1.6 mm. | 11.5 mm. |
| 2 | 1.6 mm. | 11.5 mm. |

| Teeth (mature phylloclades) | | | |
|---|---|---|---|
| Branch No. | No./Phylloclades | Center Thickness | Areole to Apex Dimension |
| 1 | 6.2 | 1.2 mm. | 5.7 mm |
| 1 | 6 | 1.1 mm. | 5.4 mm. |

Phylloclade color: Moderate olive green (7.5 GY 4/4).

The following is a general description of a flower of the new plant variety and which bloomed in December on a plant grown under shaded glasshouse nursery conditions in Winter Garden, Fla.

Bloom life: 7-9 days.

Sepaloid series of tepals:

(1) *Number.*—6.

(2) *Size (at full bloom).*—(a) Maximum base-tip dimension: 27 mm. (b) Maximum width dimensions: 17 mm.

(3) *Color.*—Translucent white basal areas of inner whorl and light yellow (2.5 Y 9/6) and/or pale yellow (2.5 Y 9/4) in marginal blade areas of inner whorl members.

Tube laminating series:

(1) *Number.*—6.

(2) *Size (at full bloom).*—(a) Maximum base-tip dimension: 52 mm. (b) Maximum width dimension: 18 mm.

(3) *Color.*—Yellowish white (10 YR 9/1) in basal areas and light yellow (5 Y 9/6) (2.5 Y 9/6) and/or pale yellow (2.5 Y 9/4) in marginal areas.

Tube forming series of tepals:

(1) *Number.*—9.

(2) *Size (at full bloom).*—(a) Perianth tube: 1. Base to keel length — 36 mm. 2. Interior major axis (at throat) — 13 mm. 3. Interior minor axis (at throat) — 8 mm. (b) Blades: 1. Maximum length (keel to tip) — 32 mm. 2. Minimum length (keel to tip) — 22 mm. 3. Maximum width — 15 mm. 4. Minimum width — 12 mm.

(3) *Color.*—(a) Perianth tube: Translucent white. (b) Blades: Translucent white basal areas and light yellow (2.5 Y 9/6) (5 Y 9/6) in marginal areas. (c) Carina (keel): Deep purplish pink (7.5 RP 6/10).

Androecium:

(1) *Stamen number.*—(a) Tube attached group: 91. (b) Basally united group: 17.

(2) *Filaments.*—(a) Color: Translucent white. (b) Size (at full bloom): 1. Length — a. Tube attached group: From 44 to 71 mm. b. Basally united group: From 45 to 56 mm. 2. Diameter — Approximately 0.5 mm.

(3) *Anthers (before dehiscing).*—Light yellow (5 Y 9/7).

Gynoecium (pistil):

(1) *Style.*—(a) Color: Strong reddish purple (2.5 RP 4/10). (b) Size (at full bloom): 1. Length — 68 mm. 2. Diameter — 1.1 mm. intermediate the opposite ends.

(2) *Stigma.*—(a) Color: Moderate purplish red (10 RP 5/8). (b) Size: About 4 mm. lobe length as measured along inner margins.

(3) *Ovary.*—(a) Color: Moderate yellow green (2.5 GY 5/6) (near 10 Y7/8). (b) Size (at full bloom): 1. Length (insertion to concavity base) — 10 mm. 2. Major axis (distal end of concavity) — 11 mm. 3. Minor axis (distal end of concavity) — 7 mm.

We claim:

1. A new and distinct plant variety of the Cactaceae family as shown and described and which is distinguished by the following combination of characteristics:

1. An erect growth habit,
2. A bloom with perianth tube forming tepals that have an axially oriented crease that extends proximally from the distal end of the tepal, and
3. A bloom with perianth tube forming and laminating tepals that in the marginal blade areas are dominated by colors with a yellow hue.

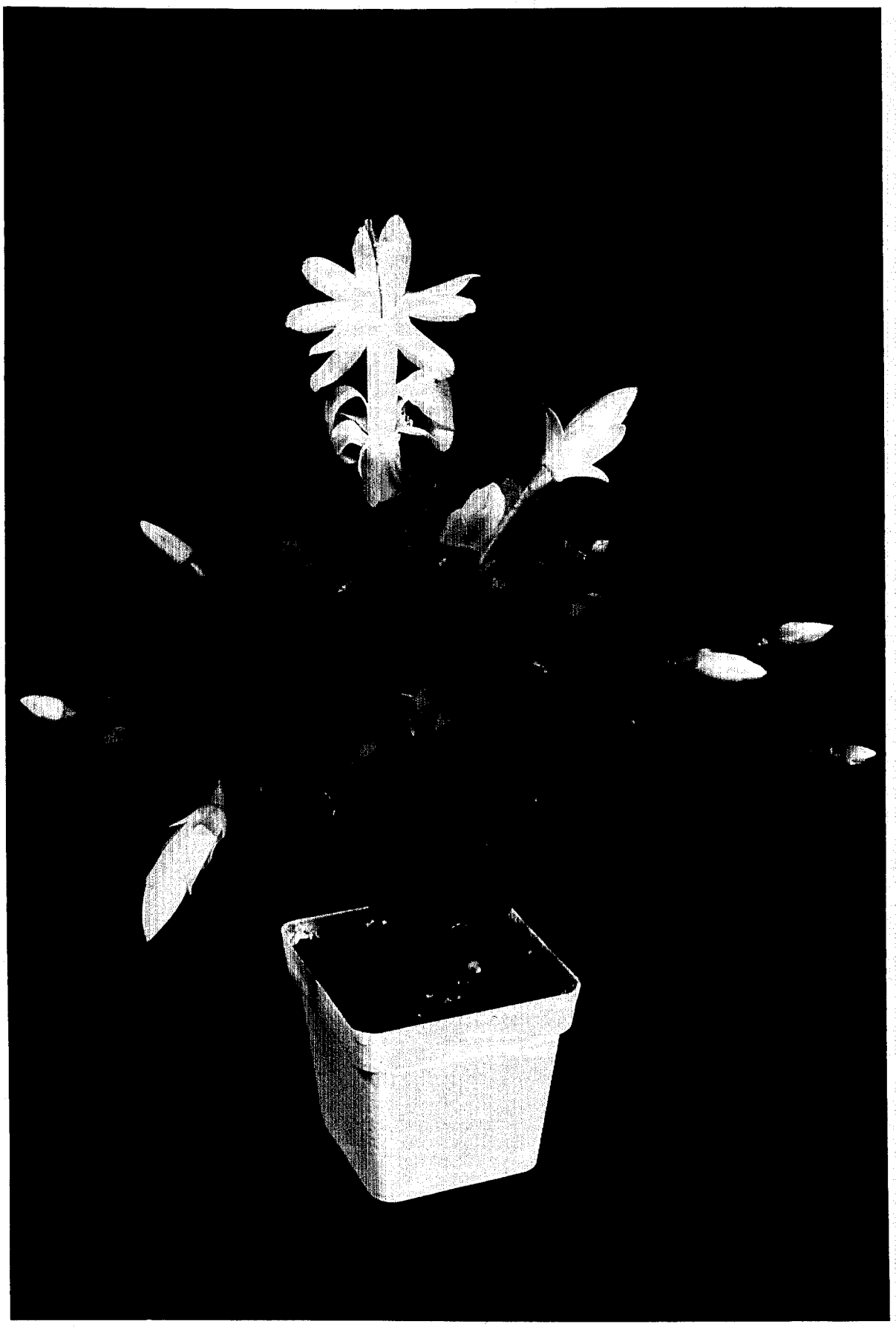

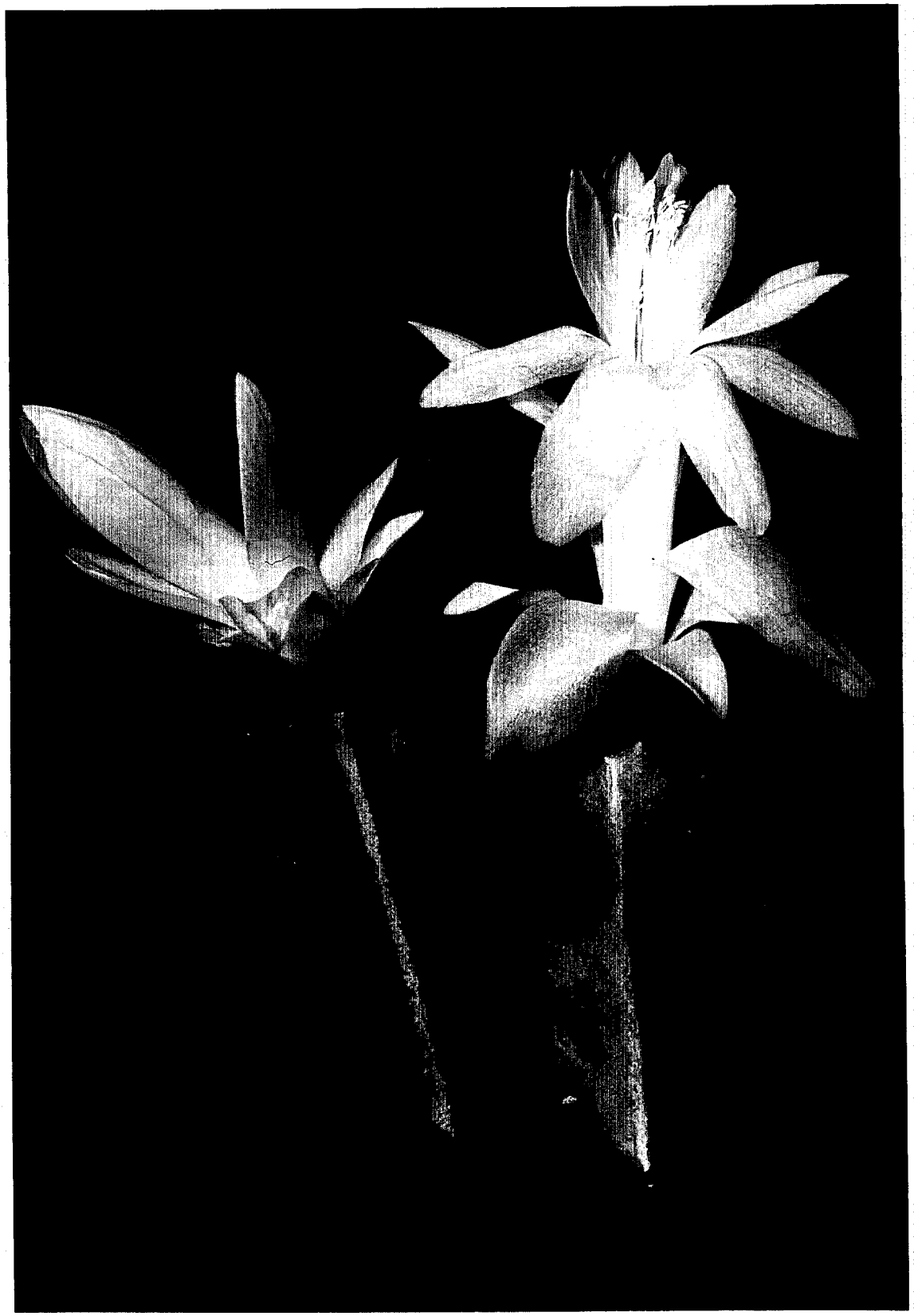

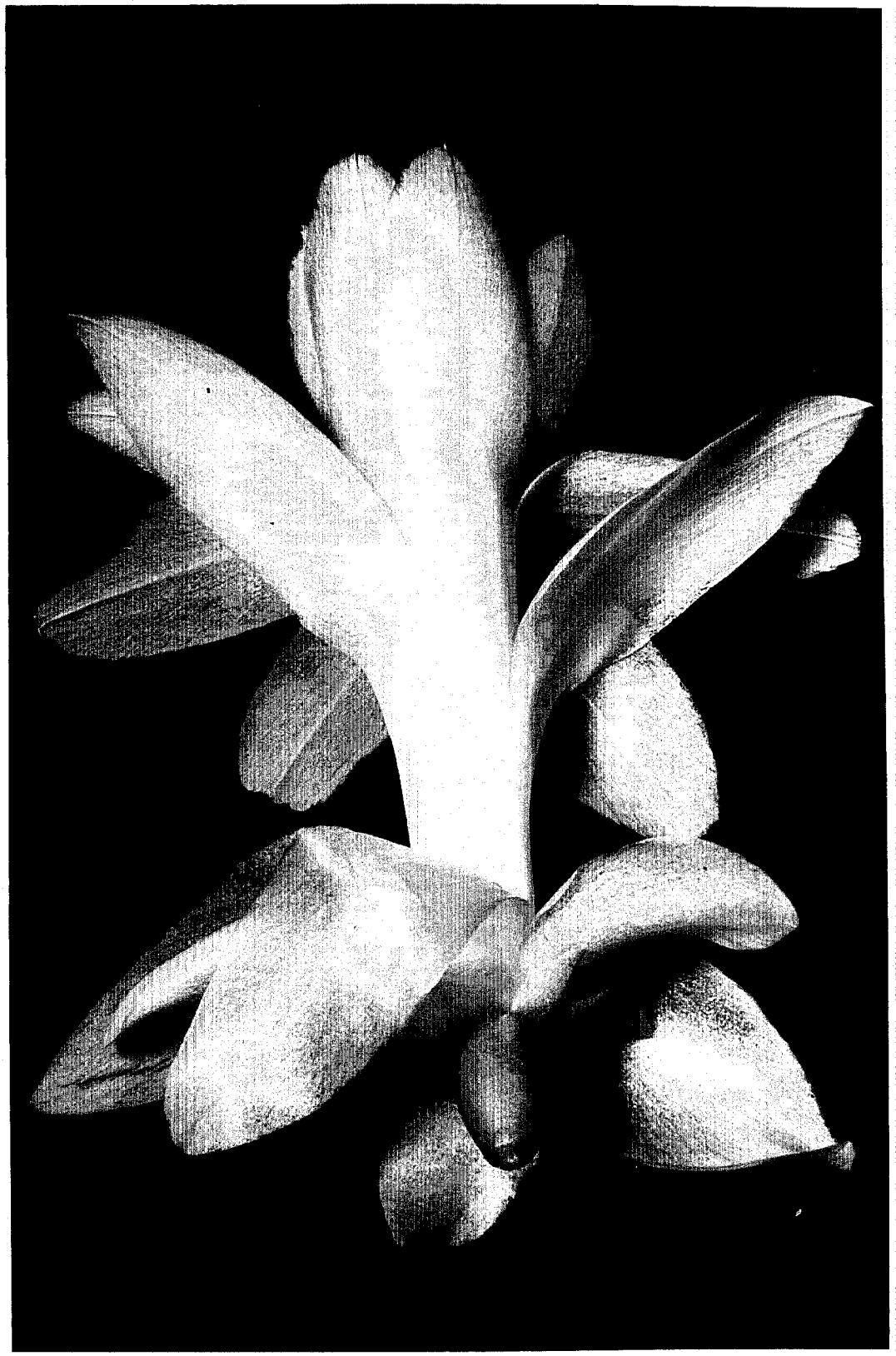

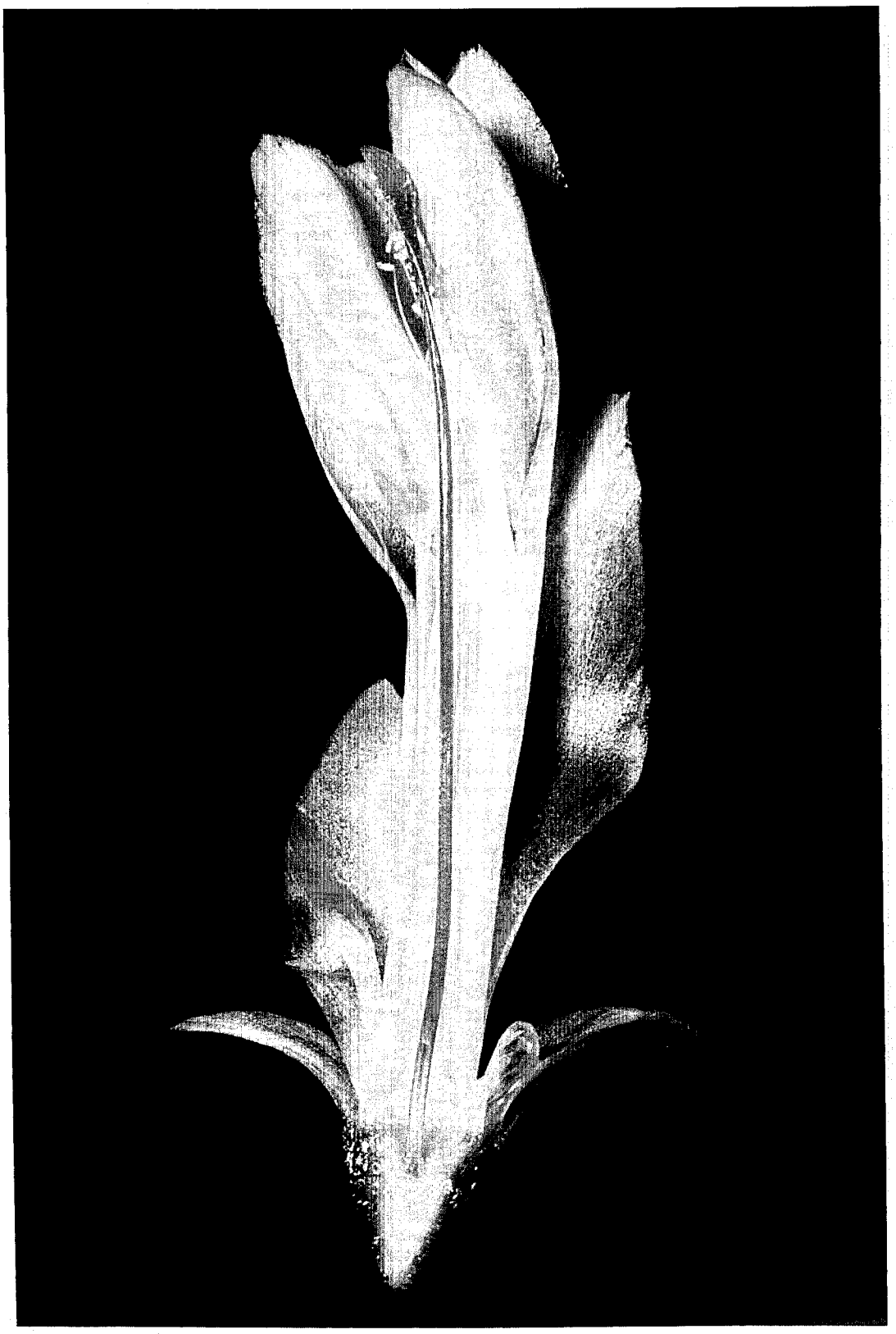

* * * * *